US 7,709,229 B2

(12) United States Patent
Casatorres Hernandez et al.

(10) Patent No.: US 7,709,229 B2
(45) Date of Patent: May 4, 2010

(54) SERUM-FREE CELL CULTURE MEDIUM FOR MAMMALIAN CELLS (75) Inventors: José Casatorres Hernandez, Madrid (ES); Carlos Martin Piera, Madrid (ES)

(73) Assignee: Ares Trading S.A., Aubonne (CH)

( * ) Notice: Subject to any disclaimer, the term of this patent is extended or adjusted under 35 U.S.C. 154(b) by 39 days.

(21) Appl. No.: 11/576,277

(22) PCT Filed: Oct. 28, 2005

(86) PCT No.: PCT/EP2005/055637

§ 371 (c)(1),
(2), (4) Date: Mar. 29, 2007

(87) PCT Pub. No.: WO2006/108455

PCT Pub. Date: Oct. 19, 2006

(65) Prior Publication Data

US 2008/0064644 A1  Mar. 13, 2008

Related U.S. Application Data

(60) Provisional application No. 60/624,885, filed on Nov. 4, 2004.

(30) Foreign Application Priority Data

Nov. 2, 2004  (EP) ................................. 04105451

(51) Int. Cl.
*C12P 21/02* (2006.01)
*C12N 15/18* (2006.01)
*C12N 5/10* (2006.01)
*C07K 14/00* (2006.01)
*C07K 14/825* (2006.01)

(52) U.S. Cl. .................... 435/70.3; 435/41; 435/69.1; 435/69.4; 435/325; 530/399

(58) Field of Classification Search ........................ None
See application file for complete search history.

(56) References Cited

U.S. PATENT DOCUMENTS

| | | | |
|---|---|---|---|
| 4,579,821 A * | 4/1986 | Palmiter et al. .......... | 435/91.41 |
| 4,767,704 A | 8/1988 | Cleveland et al. | |
| 4,935,350 A * | 6/1990 | Patel et al. ................. | 435/69.4 |
| 5,045,468 A | 9/1991 | Darfler et al. | |
| 5,122,469 A | 6/1992 | Mather et al. | |
| 5,213,980 A * | 5/1993 | Sawada et al. ............. | 435/69.4 |
| 5,316,938 A | 5/1994 | Keen et al. | |
| 5,324,656 A | 6/1994 | Ham et al. | |
| 5,811,299 A | 9/1998 | Renner et al. | |
| 6,048,728 A | 4/2000 | Inlow et al. | |
| 6,103,529 A | 8/2000 | Price et al. | |
| 6,162,643 A | 12/2000 | Wille, Jr. et al. | |
| 6,399,381 B1 | 6/2002 | Blum et al. | |
| 2003/0096402 A1 | 5/2003 | Lee et al. | |
| 2003/0096414 A1 | 5/2003 | Ciccarone et al. | |
| 2003/0153042 A1 | 8/2003 | Arnold et al. | |

FOREIGN PATENT DOCUMENTS

| | | | |
|---|---|---|---|
| EP | 0 274 445 B1 | | 7/1988 |
| EP | 0 314 317 B1 | | 5/1989 |
| EP | 0 325 224 B1 | | 7/1989 |
| EP | 0 369 458 A2 | | 5/1990 |
| GB | 2 196 348 | | 4/1988 |
| WO | WO/84/02534 | * | 7/1984 |
| WO | WO/86/04920 | * | 8/1986 |
| WO | WO 98/08934 A1 | | 3/1998 |
| WO | WO 01/16294 | | 3/2001 |

OTHER PUBLICATIONS

Lin et al., Copper Uptake in Wild Type and Copper Metallothionein-deficient Saccharomyces cerevisiae, J. Biol. Chem., 9194-9200, 1990.*
Altschul, S. F. et al. "Basic Local Alignment Search Tool", *J. Mol. Biol.*, 1990, pp. 403-410, vol. 215.
Altschul, S. F. et al. "Grapped BLAST and PSI-BLAST: A New Generation of Protein Database Search Programs", *Nucleic Acids Research*, 1997, pp. 3389-3402, vol. 25, No. 17.
Balamurugan, K. et al. "Metal-responsive Transcription Factor (MTF-1) and Heavy Metal Stress Response in Drosophila and Mammalian Cells: A Functional Comparison", *Biol. Chem.*, Jul. 2004, pp. 597-603, vol. 385.
Becker, G. W. et al. "Isolation and Characterization of a Sulfoxide and a Desamido Derivative of Biosynthetic Human Growth Hormone", *Biotechnology and Applied Biochemistry*, 1988, pp. 326-337, vol. 10.
Bewley, T. A. et al. "Sequence Comparison of Human Pituitary Growth Hormone, Human Chorionic Somatomammotropin, and Ovine Pituitary Growth and Lactogenic Hormones", *Int. J. Peptide Protein Res.*, 1972, pp. 281-287, vol. 4.
Bittel, D. et al. "The DNA Binding Activity of Metal Response Element-Binding Transcription Factor-1 Is Activated in Vivo and in Vitro by Zinc, but Not by Other Transition Metals", *The Journal of Biological Chemistry*, Mar. 20, 1998, pp. 7127-7133, vol. 273, No. 12.
Bohak, Z. et al. "Novel Anchorage Matrices for Suspension Culture of Mammalian Cells", *Biopolymers*, 1987, pp. S205-S213, vol. 26.
Carter, M. J. et al. "Are Continuous Cell Lines Safe as Substrates for Human Drugs and Biologics? A Case Study with Human Growth Hormone", *Develop. Biol. Standard*, 1989, pp. 101-107, vol. 70.
Chen, E. Y. et al. "The Human Growth Hormone Locus: Nucleotide Sequence, Biology, and Evolution", *Genomics*, 1989, pp. 479-497, vol. 4.
Denoto, F. M. et al. "Human Growth Hormone DNA Sequence and mRNA Structure: Possible Alternative Splicing", *Nucleic Acids Research*, 1981, pp. 3719-3730, vol. 9, No. 5.
Devereux, J. et al. "A Comprehensive Set of Sequence Analysis Programs for the VAX", *Nucleic Acids Research*, 1984, pp. 387-395, vol. 12, No. 1.

(Continued)

*Primary Examiner*—Gary B Nickol
*Assistant Examiner*—Elly-Gerald Stoica
(74) *Attorney, Agent, or Firm*—Saliwanchik, Lloyd & Saliwanchik (57) ABSTRACT

This invention relates to a process for the manufacturing of a protein in mammalian cells cultured in a serum-free medium.

24 Claims, 5 Drawing Sheets

OTHER PUBLICATIONS

Gertler, A. et al. "Inhibition of Lactogenic Activities of Ovine Prolactin and Human Growth Hormone (hGH) by a Novel Form of a Modified Recombinant hGH", *Endocrinology*, 1986, pp. 720-726, vol. 118, No. 2.

Goeddel, D. et al. "Direct Expression in *Escherichia coli* of a DNA Sequence Coding for Human Growth Hormone", *Nature*, Oct. 1979, pp. 544-548, vol. 281, No. 18.

Graf, L. et al. "Human Somatotrophin—Selective Removal with Trypsin of Residues 135-145 from the Hormone Molecule with No Loss of Biological Activities", *The Journal of Biological Chemistry*, Mar. 10, 1982, pp. 2365-2369, vol. 257, No. 5.

Grantham, R. et al. "Amino Acid Difference Formula to Help Explain Protein Evolution", *Science*, 1974, pp. 862-864, vol. 185.

Hsiung, H. M. et al. "Use of Bacteriocin Release Protein in *E. coli* for Excretion of Human Growth Hormone into the Culture Medium", *Bio/Technology*, Mar. 1989, pp. 267-271, vol. 7.

Jorgensen, K. D. et al. "Pharmacokinetics of Biosynthetic and Pituitary Human Growth Hormones in Rats", *Pharmacology & Toxicology*, 1988, pp. 129-134, vol. 63.

Lewis, U. J. et al. "Altered Proteolytic Cleavage of Human Growth Hormone as a Result of Deamidation", *The Journal of Biological Chemistry*, Nov. 25, 1981, pp. 11645-11650, vol. 256, No. 22.

Lewis, U. J. et al. "A Naturally Occurring Structural Variant of Human Growth Hormone", *The Journal of Biological Chemistry*, Apr. 25, 1978, pp. 2679-2687, vol. 253, No. 8.

Lewis, U. J. et al. "Enhancement of the Hyperglycemic Activity of Human Growth Hormone by Enzymic Modification", *Endocrinology*, 1977, pp. 1587-1603, vol. 101, No. 5.

Lewis, U. J. et al. "Human Growth Hormone: Additional Members of the Complex", *Endocrinology*, 1979, pp. 1256-1265, vol. 104, No. 5.

Lewis, U. J. et al. "The 20,000-Dalton Variant of Human Growth Hormone: Location of the Amino Acid Deletions", *Biochemical and Biophysical Research Communications*, Jan. 29, 1980, pp. 511-516, vol. 92, No. 2.

Martial, J. A. et al. "Human Growth Hormone: Complementary DNA Cloning and Expression in Bacteria", *Science*, Aug. 10, 1979, pp. 602-607, vol. 205.

Moore, J. A. et al. "Equivalent Potency and Pharmacokinetics of Recombinant Human Growth Hormones with or without an N-Terminal Methionine", *Endocrinology*, 1988, pp. 2920-2926, vol. 122, No. 6.

Miles, A. T. et al. "Induction, Regulation, Degradation, and Biological Significance of Mammalian Metallothioneins", *Critical Reviews in Biochemistry and Molecular Biology*, 2000, pp. 35-70, vol. 35, No. 1.

Novick, D. et al. "Interleukin-18 Binding Protein: A Novel Modulator of the Th1 Cytokine Response", *Immunity*, Jan. 1999, pp. 127-136, vol. 10.

Oka, M. S. et al. "Large-Scale Animal Cell Culture: A Biological Perspective", *Bioprocess Technol.*, 1990, pp. 71-92, vol. 10.

Pavlakis, G. N. et al. "Regulation of a Metallothionein-Growth Hormone Hybrid Gene in Bovine Papilloma Virus", *Proc. Natl. Acad. Sci. USA*, Jan. 1983, pp. 397-401, vol. 80.

Pearson, W. R. "[5] Rapid and Sensitive Sequence Comparison with FASTP and FASTA", *Methods in Enzymology*, 1990, pp. 63-98, vol. 183.

Petti, S. A. et al. "Three-Dimensional Mammalian Cell Growth on Nonwoven Polyester Fabric Disks", *Biotechnol. Prog.*, 1994, pp. 548-550, vol. 10, No. 5.

Puck, T. T. et al. "Genetics of Somatic Mammalian Cells: Long-Term Cultivation of Euploid Cells from Human and Animal Subjects", *The Journal of Experimental Medicine*, Jul. 24, 1958, pp. 945-956, vol. 108.

Rutherford, J. C. et al. "Metal-Responsive Transcription Factors That Regulate Iron, Zinc, and Copper Homeostasis in Eukaryotic Cells", *Eukaryotic Cell*, Feb. 2004, pp. 1-13, vol. 3, No. 1.

Singh, R. N. P. et al. "Modified Forms of Human Growth Hormone with Increased Biological Activities", *Endocrinology*, 1974, pp. 883-891, vol. 94, No. 3.

Thorlacius-Ussing, O. "Zinc in the Anterior Pituitary of Rat: A Histochemical and Analytical Work", *Neuroendocrinology*, 1987, pp. 233-242, vol. 45.

Vallee, B. L. et al. "The Biochemical Basis of Zinc Physiology", *The Physiological Reviews*, Jan. 1993, pp. 79-118, vol. 73, No. 1.

European Office Action, Application No. 05857769.3, Jul. 7, 2009, pp. 1-4.

* cited by examiner

SERUM-FREE CELL CULTURE MEDIUM FOR MAMMALIAN CELLS

CROSS-REFERENCE TO RELATED APPLICATION

This application is the U.S. national stage application of International Patent Application No. PCT/EP2005/055637, filed Oct. 28, 2005, which claims the benefit of U.S. Provisional Patent Application No. 60/624,885, filed Nov. 4, 2004, the disclosures of which are hereby incorporated by reference in their entireties, including all figures, tables and amino acid or nucleic acid sequences.

FIELD OF THE INVENTION

The present invention is in the field of cultivation of mammalian cells under serum-free culture conditions, in particular for cultivation of cells producing recombinant proteins such as e.g. human growth hormone (hGH).

BACKGROUND OF THE INVENTION

The present invention relates to a serum-free medium for the growth and maintenance of mammalian cells in culture.

Cell culture is widely used today for the production of various biologically active products, such as viral vaccines, monoclonal antibodies, non-antibody immuno-regulators, polypeptide growth factors, hormones, enzymes, tumor specific antigens, etc. These products are produced by normal or transformed and genetically engineered cells.

For culturing cells, in the past the culture medium was supplemented with serum, which serves as a universal nutrient for the growth and maintenance of all mammalian cell lines that produce biologically active products. Serum contains hormones, growth factors, carrier proteins, attachment and spreading factors, nutrients, trace elements, etc. Culture media usually contained up to about 10% of animal serum, such as fetal bovine serum (FBS), also called fetal calf serum (FCS).

Although widely used, serum has many limitations. It contains high levels of numerous proteins interfering with the limited quantities of the desired protein of interest produced by the cells. These proteins derived from the serum must be separated from the product during downstream processing such as purification of the protein of interest, which complicates the process and increases the cost.

The advent of BSE (Bovine Spongiform Encephalopathy), a transmissible neurodegenerative disease of, cattle with a long latency or incubation period, has raised regulatory concerns about using animal-derived sera in the production of biologically active products.

There is therefore a great demand for the development of alternative media free from animal serum that support cell growth and maintain cells during the production of biologically active products.

Generally, cell culture media comprise many components of different categories, such as amino acids, vitamins, salts, fatty acids, and further compounds.

Amino acids: For instance, U.S. Pat. No. 6,048,728 (Inlow et al.) discloses that the following amino acids may be used in a cell culture medium: Alanine, Arginine, Aspartic Acid, Cysteine, Glutamic Acid, Glutamin, Glycine, Histidine, Isoleucine, Leucine, Lysine, Methionine, Phenylalanine, Proline, Serine, Tryptophan, Tyrosine, Threonine, and Valine.

Vitamins. U.S. Pat. No. 2003/0096414 (Ciccarone et al.) or U.S. Pat. No. 5,811,299 (Renner et al.) for example describe that the following vitamins may be used in a cell culture medium, Biotin, Pantothenate, Choline Chloride, Folic Acid, Myo-Inositol, Niacinamide, Pyridoxine, Riboflavin, Vitamin B12, Thiamine, Putrescine.

Salts: For instance, U.S. Pat. No. 6,399,381 (Blum et al.) discloses a medium comprising $CaCl_2$, KCl, $MgCl_2$, NaCl, Sodium Phosphate Monobasic, Sodium Phosphate Dibasic, Sodium Selenite, $CuSO_4$, $ZnCl_2$. Another example for a document disclosing the inorganic salts that may be used in a culture medium is U.S. Pat. No. 2003/0153042 (Arnold et al.), describing a medium comprising $CaCl_2$, KCl, $MgCl_2$, NaCl, Sodium Phosphate Monobasic, Sodium Phosphate Dibasic, $CuCl_2.2H_2O$, $ZnCl_2$.

Fatty acids: Fatty acids that are known to be used in media are Arachidonic Acid, Linoleic Acid, Oleic Acid, Lauric Acid, Myristic Acid, as well as Methyl-beta-Cyclodextrin, see e.g. U.S. Pat. No. 5,045,468 (Darfler). It should be noted that cyclodextrin is not a lipid per se, but has the ability to form a complex with lipids and is thus used to solubilize lipids in the cell culture medium.

Further components, in particular used in the frame of serum-free cell culture media, are compounds such as glucose, glutamine, Na-pyruvate, insulin or ethanolamine (e.g. EP 274 445), or a protective agent such as Pluronic F68. Pluronic® F68 (also known as Poloxamer 188) is a block copolymer of ethylene oxide (EO) and propylene oxide (PO).

Standard "basic media" are also known to the person skilled in the art. These media already contain several of the medium components mentioned above. Examples of such media that are widely applied are Dulbecco's Modified Eagle's Medium (DMEM), DMEM F12 (1:1), Ham's Nutrient mixture F-10, Roswell Park Memorial Institute Medium (RPMI), MCDB 131, or William's Medium E. These commercial media are available e.g. from Gibco, Invitrogen.

Metals such as Zinc (Zn) and Copper (Cu) are involved in metabolic reactions (Vallee and Falchuk, 1993, or Lindner, 1991).

Zinc is essential to the structure and function of a large number of macromolecules and for many enzymatic reactions. It plays a catalytic, co-catalytic or structural role in the proper folding of proteins. Zn-ATP is necessary for the synthesis of pyridoxal-5-phosphate and flavin adenosine dinucleotide (FAD), two coenzymes essential for biogenic amine synthesis and monoamine oxidase metabolism.

The activity of Zinc in protecting biological structures from damage by free radicals may be due to several factors: maintaining the adequate level of metalloproteins, which are also free radical scavengers, as an essential component of superoxide dismutase, as a protective agent for thiols, and in preventing the interaction of chemical groups with Iron to form free radicals.

In addition to that, the presence of Zn prevents lipid peroxidation. Zinc is also an effector of tubulin polymerization and acts in vitro on actin filament formation and stabilization. Zinc is also a component of the Zinc finger motif of DNA binding proteins, which is a common motif in transcription proteins.

Zinc ions exist primarily in the form of complexes with proteins and nucleic acids and participate in all aspects of intermediary metabolism, transmission and regulation of the expression of genetic information, storage, synthesis and action of peptide hormones and structural maintenance of chromatin and bio-membranes.

Copper is also a trace element important for the function of many cellular enzymes. Copper ions can adopt distinct redox states, oxidized Cu (II), or reduced Cu (I), allowing the metal to play a pivotal role in cell physiology as a catalytic cofactor in the redox-chemistry of enzymes. It functions in a group of copper oxidases, which include cytochrome c oxidase, tyrosinase, dopamine-β-monooxygenase, amine oxidases and lysyl oxidase. Copper also participates in mitochrondrial respiration, iron homeostasis as a component of ceruloplasmin, free radical scavenging and elsatin crosslinking.

Serum-free media comprising metal ions such as zinc or copper ions are known in the art, e.g. from U.S. Pat. No. 6,048,728 (Inlow et al.), U.S. Pat. No. 4,767,704 (Cleveland et al.) or WO 01/16294 (Life Technologies Inc.). However, these documents do not describe a productivity-enhancing effect of these ions if added at specific concentrations to a standard production medium.

For the development and supply of biologically active products, such as therapeutic proteins or vaccines, large amounts must be produced. Suitable cells that are widely used for production of polypeptides are Chinese Hamster Ovary (CHO) cells.

CHO cells were first cultured by Puck (J. Exp. Med. 108, 945, 1958) from a biopsy of an ovary from a female Chinese hamster. From these original cells a number of sub-lines were prepared with various characteristics. One of these CHO cell lines, CHO-K1, is praline-requiring and is diploid for the dihydrofolate reductase (DHFR) gene. Another line derived from this cell line is a DHFR deficient CHO cell line (CHO DUK B11) (PNAS 77, 1980, 4216-4220), which is characterized by the loss of DHFR function as a consequence of a mutation in one DHFR gene and the subsequent loss of the other gene.

Further cells that are frequently used for the production of proteins intended for administration to humans are human cell lines such as the human fibrosarcoma cell line HT1080 or the human embryonic kidney cell line 293.

The murine C127 cell line is also highly suitable for production of recombinant proteins (Carter at al., 1989; Oka and Rupp, 1990).

One therapeutic protein of interest is growth hormone. Human growth hormone (hGH), also known as somatropin (INN) or somatotropin, is a protein hormone produced and secreted by the somatotropic cells of the anterior pituitary. Human growth hormone plays a key role in somatic growth in childhood and in metabolism in adulthood through its effects on the metabolism of proteins, carbohydrates and lipids.

Human growth hormone is a single polypeptide chain of 191 amino acids (newly et al, 1972) having two disulfide bonds, one between Cys-53 and Cys-165, forming a large loop in the molecule, and the other between Cys-182 and Cys-189, forming a small loop near the C-terminus. The DNA sequence that confirmed the amino acid sequence was reported by Martial et al (1979). Purified hGH is a white amorphous powder in its lyophilized form. It is readily soluble (concentrations >10 mg/L) in aqueous buffers at pH in a range of 6.5 to 8.5.

In solution, hGH exists predominantly as a monomer, with a small fraction as dimers and higher molecular weight oligomers. Under certain conditions, hGH can be induced to form larger amounts of dimers, trimers and higher oligomers.

Several derivatives of hGH are known, including naturally-occurring derivatives, variants and metabolic products, degradation products primarily of biosynthetic hGH and engineered derivatives of hGH produced by genetic methods. One example of a naturally-occurring derivative of hGH is GH-V, a variant of growth hormone found in the placenta. Other members of the gene locus are described in Chen et al (1989). Any derivative of hGH, including derivatives designed to be long-lasting in the body, can be used for the purpose of the present invention as long as it retains the biological activity of hGH.

Methionyl hGH was the first form of hGH to be produced through recombinant DNA technology. This compound is actually a derivative of hGH having one additional methionine residue at its N-terminus (Goeddel et al, 1979).

A naturally-occurring variant of hGH called 20-K-hGH has been reported to occur in the pituitary as well as in the bloodstream (Lewis at al, 1978; Lewis at al, 1980). This compound, which lacks the 15 amino acid residues from Glu-32 to Gln-46, arises from an alternative splicing of the messenger ribonucleic acid (DeNoto et al, 1981). This compound shares many, but not all of the biological properties of hGH.

20-K-hGH is made in the pituitary and secreted into the blood. It makes up about 5% of growth hormone output of adults, and about 20% of growth hormone output of children. It has the same growth promoting activity as 22 kD growth hormone, and has been reported to have equal to or greater the amount of lipolytic activity as the 22 kD form. It binds to growth hormone receptors with equal affinity as the 22 kb growth hormone, and has one tenth the lactogenic (prolactin-like) bioactivity as the 22 kD hormone. Unlike 22 kD, the 20-k-hGH has weak anti-insulin activity.

A number of derivatives of hGH arise from proteolytic modifications of the molecule. The primary pathway for the metabolism of hGH involves proteolysis. The region of hGH around residues 130-150 is extremely susceptible to proteolysis, and several derivatives of hGH having nicks or deletions in this region have been described (Thorlacius-Ussing, 1987). This region is in the large loop of hGH, and cleavage or a peptide bond there results in the generation of two chains that are connected through the disulfide bond at Cys-53 and Cys-165. Many of these two-chain forms are reported to have increased biological activity (Singh et al, 1974). Many derivatives of human growth hormone have been generated artificially through the use of enzymes. The enzymes trypsin and subtilisin, as well as others, have been used to modify hGH at various points throughout the molecule (Lewis et al, 1977; Graff et al, 1982). One such derivative, called two-chain anabolic protein (2-CAP), was formed through the controlled proteolysis of hGH using trypsin (Becker et al, 1989). 2-CAP was found to have biological properties very distinct from those of the intact hGH molecule, in that the growth-promoting activity of hGH was largely retained and most of the effects on carbohydrate metabolism were abolished.

Asparagine and glutamine residues in proteins are susceptible to deamidation reactions under appropriate conditions. Pituitary hGH has been shown to undergo this type of reaction, resulting in conversion of Asn-152 to aspartic acid and also, to a lesser extent, conversion of Gln-137 to glutamic acid (Lewis et al, 1981). Deamidated hGH has been shown to have an altered susceptibility to proteolysis with the enzyme subtilisin, suggesting that deamidation may have physiological significance in directing proteolytic cleavage of hGH. Biosynthetic hGH is known to degrade under certain storage conditions, resulting in deamidation at a different asparagine (Asn-149). This is the primary site of deamidation, but deamidation at Asn-152 is also seen (Becker et al, 1988). Deamidation at Gln-137 has not been reported in biosynthetic hGH.

Methionine residues in proteins are susceptible to oxidation, primarily to the sulfoxide. Both pituitary-derived and biosynthetic hGH undergo sulfoxidations at Met-14 and Met- 125 (Becker et al, 1988). Oxidation at Met-170 has also been reported in pituitary but not biosynthetic hGH. Both desamide hGH and Met-14 sulfoxide hGH have been found to exhibit full biological activity (Becker et al, 1988).

Truncated forms of hGH have been produced, either through the actions of enzymes or by genetic methods. 2-CAP, generated by the controlled actions of trypsin, has the first eight residues at the N-terminus of hGH removed. Other truncated versions of hGH have been produced by modifying the gene prior to expression in a suitable host. The first 13 residues have been removed to yield a derivative having distinctive biological properties (Gertler et al, 1986) in which the polypeptide chain is not cleaved.

Although human growth hormone was originally obtained from pituitary glands of cadavers, these preparations were not electorphoretically homogeneous, and antibodies appeared in the serum of patients treated with preparations of the order of 50% purity, the immunogenicity being attributed to inactive components. Recombinant DNA technology permitted production of an unlimited supply of hGH in a number of different systems. Purification of hGH from the culture medium is facilitated by the presence of only low amounts of contaminating proteins. In fact, it has been shown that hGH can be purified on a laboratory scale by a single purification step on a reversed-phase HPLC column (Hsiung et al (1989).

Recombinant human growth hormone, rhGH, is produced by Serono International S.A. as SEROSTIM®, which product has been given accelerated FDA approval for treating weight loss and wasting in AIDS patients, SAIZEN® is recombinant human growth hormone indicated for GH deficiency in children, for Turner syndrome in girls, as well as chronic renal failure in children. PROTROPIN®, produced by Genentech, Inc. (South San Francisco, Calif.), differs slightly in structure from natural sequence hGH, having an additional methionine residue at the N-terminus. Recombinant hGH is generally marketed as vials containing hGH plus additional excipients, e.g., glycine and mannitol, in a lyophilized form. A companion diluent vial is provided, allowing the patient to reconstitute the product to the desired concentration prior to administration of the dose. Recombinant hGH can also be marketed in other well-known manners, such as prefilled syringes, etc.

In general, no significant differences have been observed in the pharmacokinetics or biological activities of recombinant natural sequence hGH, recombinant N-methionyl-hGH, or pituitary-derived material in humans (Moore et al, 1988; Jorgensson et al, 1988).

In view of the various medical indications for which growth hormone is used, there is a need for an efficient and safe way of producing sufficient quantities of it in cell culture, in particular in a serum-free cell culture process.

Serum-free media have been described in the art.

For instance, U.S. Pat. No. 6,162,643 describes a serum-free basal medium designated HECK-109, containing trace amounts of Copper Sulphate and Zinc Chloride. This medium is specifically designed for primary and secondary cultures of normal human cells such as keratinocytes with the aim of tissue generation for human transplantation. Expression of recombinant human proteins in cell lines in vitro is not mentioned in this U.S. patent.

U.S. Pat. No. 5,324,666 discloses a serum-free basal medium called MCDB120 and MCDB 131M, comprising trace amounts of Copper Sulphate and Zinc Chloride. This medium is specifically designed for the in vitro culture of human muscle satellite cells with the aim of preventing differentiation of these cells. Production of recombinant human proteins is not envisaged in the frame of this document.

GB 2 196 348 describes a synthetic medium for the in vitro culture of hybridoma and myeloma cells. The medium contains Copper, Zinc and Ferric ions, Cultivation of the hybridoma or myeloma cells in this medium is exclusively for the purpose of manufacturing monoclonal antibodies.

U.S. Pat. No. 6,103,529 provides for a serum-free cell culture medium formulation for the in vitro cultivation of animal cells. The animal cells may be used for the production of viruses, monoclonal antibodies, hormones or growth factors. However, the production of growth hormone is not mentioned in this document.

U.S. Pat. No. 6,048,728 discloses a protein-free cell culture medium comprising Co-, Zn- and Fe-ions for the cultivation of animal cells in order to produce e.g. natural or recombinant products, such as antibodies. Such products to be produced by the cultured cells do not include growth hormones or growth factors, which are exclusively mentioned as constituents of the serum-free medium in order to enhance cell growth of in culture.

U.S. Pat. No. 5,316,938 discloses a biochemically defined culture medium for Chinese Hamster Ovary (CHO) cells comprising Ferric Citrate, Zinc sulphate and Copper sulphate, named WCM5. The medium is specifically designed for antibody and tPA production in CHO cells.

U.S. Pat. No. 5,122,459 describes a method for production of recombinant proteins in a serum-free culture medium containing Zinc and Ferric ions, particularly suitable for the culture of CHO cells. Production of growth hormone is not mentioned in this document.

Therefore, the problem underlying the present invention is providing a serum-free cell culture medium for the efficient production of Growth Hormone, in particular human Growth Hormone (hGH).

SUMMARY OF THE INVENTION

The present invention is based on the development of a cell culture medium that is free from components derived from animal serum and at the same time highly effective for cell growth and maintenance of mammalian cells in culture, particularly allowing production of recombinant proteins.

Therefore, in a first aspect, the invention relates to a cell culture medium free from components derived from animal serum, comprising Zinc and/or Copper, in trace amounts. Preferably, the medium of the invention further comprises Ferric ions in trace amounts.

In a second aspect, the invention relates to a process for production of a protein comprising the step of culturing a cell expressing a protein of interest in the medium of the invention.

A third aspect of the invention relates to the use of a medium according to the invention for the production of a protein of interest.

A fourth aspect of the invention relates to the use of a medium according to the invention for the maintenance of cells in culture during production phase of a polypeptide of interest.

DETAILED DESCRIPTION OF THE INVENTION

The present invention is based on the development of a cell culture medium that is free from animal serum.

In accordance with the present invention, the cell culture medium free from animal serum comprises:

Zinc (Zn) in a concentration ranging from 0.2 to 1.75 µM, and/or

Copper (Cu) in a concentration ranging from 10 to 75 nM, and/or

Ferric ions (Fe) in a concentration ranging from 3 to 10 µM.

As shown in the Examples below, addition of Zn and/or Cu in trace amounts to a standard medium resulted in increase of productivity of cells expressing a secreted protein of interest.

The addition of both Zn and Cu in the above-identified concentrations led to an increase in productivity of recombinant human growth hormone (GH) in C127 cells of over 60% of the control (same cells cultured in standard DMEM). When the GH expressing cells were cultured in a medium comprising Zn, Cu and, Fe ions in the above-identified concentrations, the productivity was increased by about 70% as compared to the control.

Preferred concentration ranges of the metal ions of the medium of the invention are as follows:

Zinc at about 0.2, 0.25, 0.30, 0.35, 0.40, 0.45, 0.5, 0.55, 0.60, 0.65, 0.70, 0.75, 0.80, 0.85, 0.90, 0.95, 1, 1.05, 1.1, 1.15, 1.2, 1.25, 1.3, 1.35, 1.4, 1.45, 1.5, 1.55, 1.6, 1.65, 1.7, 1.75 µM.

Preferably, zinc is comprised at about 0.5 µM or about 1.5 µM. It is also preferred that zinc is comprised as zinc sulfate.

Copper at about 10, 15, 20, 25, 30, 35, 40, 45, 50, 55, 60, 65, 70, or 75 nM.

Preferably, copper is comprised at about 25 nM. It is also preferred that Copper is comprised as copper sulfate.

Ferric ions are comprised at about 1, 1.5, 2, 2.5, 3, 3.5, 4, 4.5, 4.8, 5, 5.5, 6, 6.5, 7, 7.5, 8, 8.5, 9, 9.5 or 10 µM.

Preferably, ferric ions are comprised at about 5 or 6 µM. Ferric ions may preferably be comprised as ferric citrate and/or ferric nitrate, and it is further preferred that ferric citrate accounts for most of the ferric ions comprised in the cell culture medium. The medium may comprise, for example, about 5 µM of ferric citrate and about 1 µM of ferric nitrate.

In a preferred embodiment, the medium further comprises the components of a basic medium. It is preferred that the medium contains Dulbecco's Modified Eagle's Medium (DMEM) as basic medium. The composition of standard DMEM is reported in the example below.

The second aspect of the present invention relates to a process for production of a protein comprising the step of culturing a cell expressing a protein of interest in the medium of the invention.

The culturing step of the process of the invention may be carried out in any suitable environment, such as Petri dishes, T-flasks or roller bottles, but may also be done in vessels having greater volumes such as e.g. a bioreactor.

The protein of the invention may be expressed using any promoter that is suitable in the particular cell type used. In a highly preferred embodiment, the protein is expressed from the metallothionein (MT) promoter. If murine cells are used for protein production, the promoter is preferably the murine MT-1 promoter.

Preferably, the process further comprises the step of collecting the medium comprising the protein of interest.

In a preferred embodiment, the process further comprises isolating the protein of interest.

In a further preferred embodiment, the process further comprises formulating the isolated protein with a pharmaceutically acceptable carrier to obtain a pharmaceutical composition.

In a third aspect, the invention relates to the use of the medium according to the invention for the production of a polypeptide of interest.

In a fourth aspect, the invention relates to the use of a medium of the invention for the maintenance of cells in culture during production phase of a polypeptide of interest.

The cells to be used in the frame of the various aspects of the present invention are preferably mammalian cells. They may be of human or animal origin. Examples of mammalian cells that can be cultured in the process according to the present invention include, e.g., murine C127 cells, 3T3 cells, COS cells, human osteosarcoma cells, MRC-5 cells, BHK cells, VERO cells, CHO (Chinese hamster ovary) cells, HEK 293 cells, rHEK 293 cells, normal human fibroblast cells, Stroma cells, Hepatocytes cells, or PER.C6 cells. Examples of hybridomas that may be cultured in the process according to the present invention include, e.g., DA4.4 cells, 123A cells, 127A cells, GAMMA cells and 67-9-B cells.

It is preferred to culture murine C127 cells in accordance with the present invention.

The cells cultured in accordance with the present invention may grow in suspension or, for anchorage dependent cells, attached to a solid support. Microcarriers and Fibra-Cel® disks are used in mammalian cell culture for the growth of anchorage-dependent cells and are among the established technological platforms for industrial production of proteins (see, e.g., Bohak et al. 1987; Petti et al 1994).

The process of the invention preferably serves to produce a polypeptide of interest. The medium of the invention is thus used for the production of a polypeptide or protein of interest, which may be any polypeptide for which production is desired, either small-scale or large-scale.

The polypeptide of interest may be e.g. a naturally secreted protein, a normally cytoplasmic protein, a normally transmembrane protein, or a human or a humanized antibody. When the protein of interest is a naturally cytoplasmic or a naturally transmembrane protein, the protein has preferably been engineered in order to become soluble and secreted, i.e. by placing a signal peptide in front of it or of a (soluble or extracellular) fragment of it.

The polypeptide of interest may be of any origin. Preferred polypeptides of interest are of human origin, and more preferably, the proteins of interest are therapeutic proteins.

Preferably, the protein of interest is selected from a hormone, a cytokine-binding protein, an interferon, a soluble receptor, or an antibody.

Therapeutic proteins that may be produced according to a method of the present invention include, e.g., chorionic gonadotropin, follicle-stimulating hormone, lutropin-choriogonadotropic hormone, thyroid stimulating hormone, growth hormone, in particular human growth hormone, interferons (e.g., interferon beta-1a, interferon beta-1b), interferon receptors (e.g., interferon gamma receptor), TNF receptors p55 and p75, and soluble versions thereof, TAC1 receptor and Fc fusion proteins thereof, interleukins (e.g., interleukin-2, interleukin-11), interleukin binding proteins (e.g., interleukin-18 binding protein), anti-CD11a antibodies, erythropoietin, granulocyte colony stimulating factor, granulocyte-macrophage colony-stimulating factor, pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, Factor VIII, somatropin, bone morphogenetic protein-2, platelet-derived growth factor, hirudin, epoietin, recombinant LFA3/IgG1 fusion protein, glucocerebrosidase, and muteins, fragments, soluble forms, functional derivatives, fusion proteins thereof.

In preferred embodiments, the polypeptide is selected from the group consisting of chorionic gonadotropin (CG), follicle-stimulating hormone (FSH), lutropin-choriogonadotropic hormone (LH), thyroid stimulating hormone (TSH), human growth hormone (hGH), interferons (e.g., interferon beta-1a, interferon beta-1b), interferon receptors (e.g., interferon gamma receptor), TNF receptors p55 and p75, interleukins (e.g., interleukin-2, interleukin-11), interleukin binding proteins (e.g. interleukin-18 binding protein), anti-CD11a antibodies, and muteins, fragments, soluble forms, functional derivatives, fusion proteins thereof.

Further preferred polypeptides of interest include, e.g., erythropoietin, granulocyte colony stimulating factor, granulocyte-macrophage colony-stimulating factor, pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, Factor VIII, somatropin, bone morphogenetic protein-2, platelet-derived growth factor, hirudin, epoietin, recombinant LFA-3/IgG1 fusion protein, glucocerebrosidase, and muteins, fragments, soluble forms, functional derivatives, fusion proteins thereof.

Should the protein of interest that is produced in the process of the invention be formulated with a pharmaceutically acceptable carrier, the result of the process is a pharmaceutical composition.

The definition of "pharmaceutically acceptable" is meant to encompass any carrier, which does not interfere with the effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The pharmaceutical composition formulated according to the invention may then be administered to an individual in a variety of ways. The routes of administration include intradermal, transdermal (e.g. in slow release formulations), intramuscular, intraperitoneal, intravenous, subcutaneous, oral, intracranial, epidural, topical, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

In accordance with the present invention, it is highly preferred to use the medium of the invention for production of growth hormone.

GH may be native, i.e. naturally occurring GH. Preferably, the GH to be produced is of human origin. Since GH is a soluble, secreted protein, it is released into the cell culture supernatant, either by means of its natural signal peptide, or by means or a heterologous signal peptide, i.e. a signal peptide derived from another secreted protein which may be more efficient in the particular expression system used.

The term "growth hormone" is used herein synonymously with "GH". This term includes natural or native GH, recombinantly produced GH as well as the GH variants explained in detail in the "Background of the Invention". The term "GH", as used herein, further includes muteins, functional derivatives, active fractions, fused proteins, circularly permutated proteins and salts of GH. GH is preferably human, but may also be derived from other species, in particular mammals.

As used herein the term "muteins" refers to analogs of an GH, in which one or more of the amino acid residues of a natural GH are replaced by different amino acid residues, or are deleted, or one or more amino acid residues are added to the natural sequence of an GH, without diminishing considerably the activity of the resulting products as compared with the wild type GH. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to DNA or RNA, which encodes a GH under stringent conditions. DNAs encoding GH are known in the prior art. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-walled global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990).

Any such mutein preferably has a sequence of amino acids sufficiently duplicative of that of an GH, such as to have substantially similar activity to GH. One activity of GH is its capability of binding the GH receptor. As long as the mutein has substantial binding activity to the GH receptor (GHR), it can be considered to have substantially similar activity to GH. Thus, it can be determined whether any given mutein has substantially the same activity as GH by means of routine experimentation comprising subjecting such a mutein, e.g., to a simple sandwich competition assay to determine whether or not it binds to an appropriately labeled GHR or cells expression GHR, such as radioimmunoassay or ELISA assay.

In a preferred embodiment, any such mutein has at least 40% identity or homology with the amino acid or DNA sequence of a GH. These sequences are known in the art, e.g. from DeNoto et al, 1981 or Martial et al., 1979.

More preferably, it has at least 50%, at least 60%, at least 70%, at least 80% or, most preferably, at least 90% or 95% identity or homology thereto.

Preferred changes for muteins in accordance with the present invention are what are known as "conservative" substitutions. Conservative amino acid substitutions of GH polypeptides, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

The term "fused protein" refers to a polypeptide comprising GH, or a mutein or fragment thereof, fused with another protein, which, e.g., has an extended residence time in body fluids. GH may thus be fused to another protein, polypeptide or the like, e.g., an immunoglobulin or a fragment thereof. Fc portions of IgGs are suitable for preparation of immunoglobulin-fusion proteins. Ig fusion proteins are described for example in EP 314 317 A1 (Genentech) or EP 0 325 224 A2 (Zymogenetics Inc.).

As "active fractions" of an GH, or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to GH.

Should the GH of the Invention be used as a pharmaceutical composition, such pharmaceutical composition may be used for treatment and/or prevention of a number of diseases or disorders. Such diseases or disorders are preferably related to insufficient endogenous GH production. Purified GH may be used e.g. for treatment and/or prevention GH deficiency, AIDS wasting, lipodystrophy (also called HARS-HIV-associated dysmorphia/dysmetabolic syndrome), or short bowel syndrome, in particular pediatric. Further diseases in which administration of growth hormone may be indicated include liver cirrhosis, adult growth deficiency, atherosclerosis, Crohn's disease and Ulcerative Colitis, osteoarthritis, cardiac cachexia, congestive Heart Failure, chronic renal insufficiency, blood colt reconstitution or mobilization, male infertility, hematopoietic stem cell mobilization, multiple sclerosis, stroke, Multiple System Atrophy, or cancer.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentations without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLE

Development of a New Serum-Free Production Medium for hGH Expressing C127 Cells

1. Introduction

This study describes the experimental work relating to the development of a production culture medium (DMEM, "*Dulbecco's Modified Eagle's Medium*") by addition of trace metallic elements. As result of this development, a remarkable increase of the r-hGH productivity in the C127 cell cultures was obtained.

The following table 1 summarizes the composition of DMEM and the development that will be presented in the frame of this example.

TABLE 1

Formulation of growth medium, DMEM and production medium.

| COMPONENTS | Growth medium, mg/L | DMEM, mg/L | Production medium, mg/L |
|---|---|---|---|
| AMINO ACIDS | | | |
| L-ALANINE | 49.45 | | |
| L-ARGININE HCL | 227.5 | 84.0 | 84.0 |
| L-ASPARAGINE $H_2O$ | 27.50 | | |
| L-ASPARTATE | 21.65 | | |
| L-CYSTEINE HCl $H_2O$ | 17.56 | | |
| L-CYSTINE 2HCl | 31.29 | 62.0 | 62.0 |
| L-GLUTAMATE | 40.35 | | |
| L-GLUTAMINE | 693.5 | 584.0 | 584.0 |
| GLYCINE | 43.75 | 30.0 | 30.0 |
| L-HISTIDINE HCl, $H_2O$ | 41.48 | 42.0 | 42.0 |
| L-HYDROXYPROLINE | 6.50 | | |
| L-ISOLEUCINE | 114.5 | 105.0 | 105.0 |
| L-LEUCINE | 119.1 | 105.0 | 105.0 |
| L-LYSINE-HCL | 151.3 | 146.0 | 146.0 |
| L-METHIONINE | 52.24 | 30.0 | 30.0 |
| L-PHENYLALANINE | 70.48 | 66.0 | 66.0 |
| L-PROLINE | 37.25 | | |
| L-SERINE | 39.25 | 42.0 | 42.0 |
| L-THREONINE | 93.45 | 95.0 | 95.0 |
| L-TRYPTOPHAN | 15.02 | 16.0 | 16.0 |
| L-TYROSINE 2Na $2H_2O$ | 75.79 | 104.0 | 104.0 |
| L-VALINE | 92.85 | 93.0 | 93.0 |
| SALTS | | | |
| CALCIUM CHLORIDE | 121.0 | 200 | 200 |
| $Fe(NO_3)_3 \cdot 9H_2O$ | 0.050 | 0.1 | 0.1 |
| FERROUS SULFATE $7H_2O$ | 1.251 | | |
| KCl | 334.2 | 400 | 400 |
| MAGNESIUM CHLORIDE | 40.94 | | |
| $MgSO_4$ ANHYDROUS | 48.84 | 97 | 97 |
| $Na_2HPO_4$ | 71.02 | | |
| SODIUM SELENITE $5H_2O$ | 0.030 | | |
| NaCl | 7500 | 6400 | 6400 |
| $NaH_2PO_4$ $H_2O$ | 62.5 | 125 | 125 |
| $NaHCO_3$ | 1200 | 3700 | 3700 |
| LITHIUM CHLORIDE | 1.00 | | |
| $ZnSO_4 \cdot 7H_2O$ | 0.432 | | 0.144 |
| CARBOHYDRATES | | | |
| D-GLUCOSE | 3650 | 4500 | 4500 |
| VITAMINS | | | |
| ASCORBIC ACID | 0.500 | | |
| BIOTIN | 0.1035 | | |
| CHOLINE CHLORIDE | 11.48 | 4.00 | 4.00 |
| VITAMIN B12 | 1.68 | | |
| D Ca PANTHOTENATE | 2.34 | 4.00 | 4.00 |

TABLE 1-continued

Formulation of growth medium, DMEM and production medium.

| COMPONENTS | Growth medium, mg/L | DMEM, mg/L | Production medium, mg/L |
|---|---|---|---|
| FOLIC ACID | 3.65 | 4.00 | 4.00 |
| I-INOSITOL | 17.1 | 7.00 | 7.00 |
| NIACINAMIDE | 2.27 | 4.00 | 4.00 |
| PARA-AMINO-BENZOIC ACID | 1.00 | | |
| PYRIDOXAL-HCl | 0.25 | 4.00 | 4.00 |
| PYRIDOXINE HCl | 4.531 | | |
| RIBOFLAVINE | 0.419 | 0.40 | 0.40 |
| THIAMINE HCl | 2.92 | 4.00 | 4.00 |
| LIPIDS | | | |
| LINOLEIC ACID | 0.042 | | |
| LIPOIC ACID | 0.205 | | |
| METHYL LINOLEATE | 0.1 | | |
| MISCELLANEOUS | | | |
| FERRIC CITRATE | 122.5 | | 1.22 |
| HEPES | 3600 | | |
| HYPOXANTHINE | 2.900 | | |
| IRON(II) d-GLUCONATE DIHYDRATE | 4.820 | | |
| L-GLUTHATIONE | 0.500 | | |
| MERCAPTOETHANOL | 0.234 | | |
| SODIUM PYRUVATE | 57.00 | 110.0 | 110.0 |
| PUTRESCINE, 2HCl | 0.241 | | |
| THYMIDINE | 0.505 | | |
| DETERGENTS | | | |
| ETHANOLAMINE (as base) | 6.25 | | |
| TRACE ELEMENTS | | | |
| SILVER CHLORIDE | 0.0000044 | | |
| BARIUM CHLORIDE $2H_2O$ | 0.002 | | |
| COBALT CHLORIDE $6H_2O$ | 0.002 | | |
| CHROMIC POTASSIUM SULFATE | 0.001 | | |
| POTASSIUM BROMIDE | 0.0001 | | |
| POTASSIUM IODIDE | 0.0001 | | |
| MOLYBDIC ACID (Ammonium Molybdate $4H_2O$) | 0.0001 | | |
| SODIUM FLUORIDE | 0.004 | | |
| AMMONIUM METAVANADATE | 0.0006 | | |
| NICKEL NITRATE $6H_2O$ | 0.0002 | | |
| RUBIDIUM CHLORIDE | 0.00001 | | |
| STANNOUS CHLORIDE $2H_2O$ | 0.0001 | | |
| COPPER SULFATE•$5H_2O$ | 0.0064 | | 0.0064 |
| MANGANESE CHLORIDE $4H_2O$ | 0.0001 | | |
| TITANIUM OXYDE | 0.001 | | |
| SUPPLEMENTS | | | |
| HUMAN RECOMBINANT INSULIN | 10 mg/L | | |
| PHYSICAL ADJUSTMENTS | | | |
| pH | 7.1 ± 0.1 | 7.0 ± 0.2 | 7.0 ± 0.2 |
| OSMOLARITY (mosm/kg) | 325 ± 25 | 330 ± 30 | 330 ± 30 |

2. Materials and Methods

Reagents and Solutions

All chemical reagents were obtained form Merck®: Zinc sulfate ($ZnSO_4.7H_2O$), Copper Sulfate ($CuSO_4.5H_2O$), Barium Chloride ($BaCl_2.2H_2O$), Cobalt Chloride ($CoCl_2.6H_2O$), Chromium Potassium Sulfate (K[Cr$(SO_6H_4)_2$ $(H_2O)_2$].$6H_2O$), Nickel Nitrate (Ni$(NO_3)_2$.$6H_2O$), Sodium Selenite ($Na_2SeO_3$.$5H_2O$). Ferric Citrate ($FeC_6H_5O_7$ Sigma® catalogue number F3388) was used as an iron source.

Growth medium trace elements mixture (100,000×) was provided by JRH® Biosciences.

All trace element solutions to be assayed were prepared as concentrated solutions in distilled water and sterilized by filtration through a 0.2 μm filter.

The addition of the different supplements assayed (metal solutions etc.) in different experiments was carried out directly on fresh culture medium.

Cell Cultures

Genetically modified C127 murine cells (ATCC CRL 1616) were used for the expression of the recombinant human growth hormone (rhGH). The vector is based on BPV69T comprising the pBR322 multiple cloning site and comprising 1.6 kb of the rhGH minigene under the control of mouse metallothionein-1 (MT-1) promoter. Cultures derived from one Working Cell Bank obtained from different rhGH production batches were used in the experiments.

Cell cultures were kept incubated at 36° C.±0.5° C. and 0.4 rpm in 2125 cm² roller bottles containing 375 mL±15 mL of culture medium or in 1700 cm cm² roller bottles containing 300 mL of culture medium.

Culture Medium

Culture medium used for the rhGH production phase was DMEM with 4.5 g/L glucose buffered with sodium bicarbonate (3.7 g/L).

RHGH Titration

Measurement of rhGH in the culture medium was carried out daily by reverse-phase HPLC titration:

Materials

Synchropak RP4, 100×4.6 mm i.d., 300 Å Cat #C4R103-10 (Eichrom).

Resource RPC 1 mL, 30 mm×6.4 mm i.d., 15 µm, art 17-1181-01, Amersham Biosciences.

Symmetry 300, 50 mm×4.6 i.d., C4 5 µm, P/N 186000287 (Waters).

Reagents

Trifluoroacetic acid (TFA) (Pierce, Cat #28904 or equivalent).

Acetonitril (ACN) (Merck 1.00030 or equivalent).

Purified water, PW (e.g. MilliQ water, or equivalent),

Helium

Solutions

Mobile Phase A: TFA 0.08% in $H_2O$ (v/v)

Measure in a graduated flask the volume of PW water and add TFA according to the following table. Agitate and label.

| VOLUME PHASE A | VOLUME MILLIQ Water | VOLUME TFA |
|---|---|---|
| 1 L | 1 L | 0.8 Ml |
| 0.5 L | 0.5 L | 0.4 mL |
| 0.25 L | 0.25 L | 0.2 mL |

Mobile Phase B: TFA (3.08% in Acetonitrile (v/v)

Measure in a volumetric flask the volume of PW water and add TFA according to the following table. Agitate and label.

| VOLUME PHASE B | VOLUME ACN | VOLUME TFA |
|---|---|---|
| 1 L | 1 L | 0.8 mL |
| 0.5 L | 0.5 L | 0.4 mL |
| 0.25 L | 0.25 L | 0.2 mL |

Chromatography conditions are:

Elution by gradient: starting with a mixture phase A/phase B 60/40 ending at phase A/phase B 20/80. Gradient complete in 5 minutes (slightly variable depending on instrumentation in use)

Injection volume 50 µliters

Detection: UV absorbance at 215 nm.

Calibration curve: r-hGH standard at 10, 50, 100, 120 and 150 µg/ml

The r-hGH concentration of a sample is determined by comparison with standard r-hGH concentrations.

GH Productivity

Productivity is expressed as mg or rhGH per roller bottle. Raw data are rhGH concentration in the harvest (as measured by HPLC) and total number of roller bottles harvested. Typically a roller bottle during harvest phase contains around $10^9$ cells.

3. Results

In a first series of experiments, the effect of high cobalt concentration (20 µM $CoCl_2.6H_2O$) when intermittently added to the culture medium was assayed. Addition was carried out during the two medium changes in the initial step (rinse and PM=production medium, i.e. 0 point of the harvest phase) and in the intermediate step (harvests 6 and 7) of the production phase of one batch. The results (not shown) suggested that the promoter is active and can be modulated.

The elevated productivity was further confirmed with other metallic elements, Assays with 10 µM concentrations of barium ($BaCl_2 \cdot 2H_2O$), Cobalt ($CoCl_2 \cdot 6H_2O$), Chromium ($K[Cr(SO_3H_4)_2(H_2O)_2] \cdot 6H_2O$) and Nickel ($Ni(NO_3)_2 \cdot 6H_2O$), continuously added to the medium, respectively, were carried out. The results of this experiment are depicted in FIGS. 1 and 2.

Figure 1:
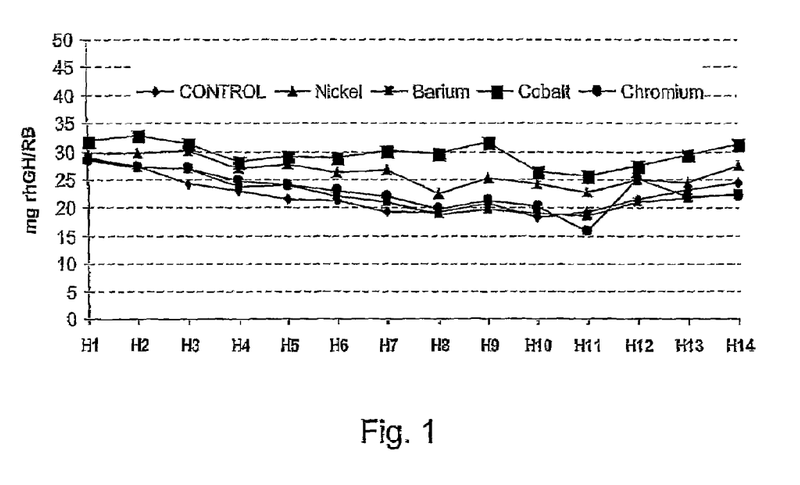
FIG. 1 shows the rhGH productivity profile obtained in the production phase under continuous addition of different elements at 10 μM into DMEM culture medium (RB=roller bottle, H1-H14=production phase days 1 to 14)
Figure 2:
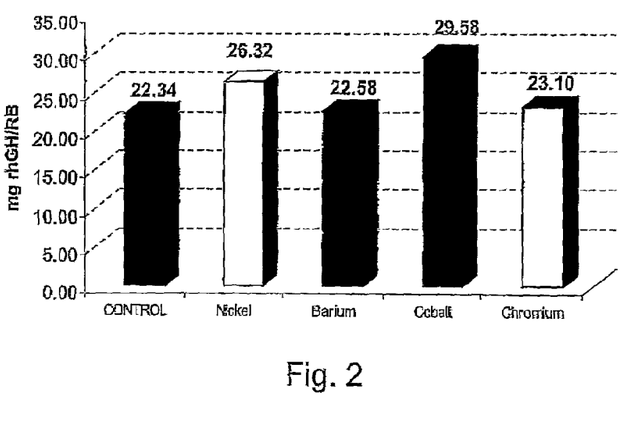
FIG. 2 shows the average rhGH productivity values, expressed as mg rhGH per roller bottle, obtained in the production phase under continuously adding of metals (Nickel, Barium, Cobalt, Chromium) at 10 µM into DMEM culture medium.

FIG. 1 shows the amount of hGH secreted by hGH expressing C127 cells when cultured in medium containing the assayed elements over the time of the experiment (14 days). FIG. 2 shows the average productivity values reached for each assayed element. Average productivity increase percentages obtained compared to control value, without trace elements, ranged between 1.1% for Barium and 32.4% for Cobalt. It was also noted that the rhGH productivity raised from 9% to 32.5% compared to control values when assayed at continued versus intermittent induction with cobalt. Neither Barium nor Chromium showed productivity increase at the assayed concentrations in DMEM.

Measurement of Individual Trace Elements

DMEM was supplemented with trace elements of Zn, Cu, Se and Co at the concentrations reported below in table 2. These concentrations correspond to the concentrations of the metal elements in growth medium. The increase in rhGH productivity achieved by supplementing DMEM with the trace elements is indicated in Table 2.

TABLE 2 rhGH productivity percentage increase when assaying the metallic ions in DMEM at the indicated µM concentrations.

| Ion | CONCENTRATION (µM) | % INCREASE OF PRODUCTIVITY |
|---|---|---|
| Zn | 1.50300 | 12.10% |
| Cu | 0.02560 | 37.50% |
| Se | 0.11400 | −3.10% |
| Co | 0.00840 | −3.20% |

It should be noted that in the case of Zinc, the assayed concentration of 1.5 µM caused a "peeling-off" phenomenon, i.e. a detachment of the cell monolayer from the plastic substrate of the roller bottles. In some cases this peeling led to a loss of the cultures in the last harvesting steps (usually between harvests 12-14). The peeling-off phenomenon can be obviated by using adequate cell culture vessels, such as the roller bottles available from Corning® under the trade name Cellbind®.

Measurement of Interactions Between Metals

Based on the effects of Copper and Zinc on the productivity of hGH production, factorial design experiments were carried out to assay the possible combined effect of the metals.

The statistical analysis of the results is shown in table 3. A strong synergic effect on the productivity ($p \leq 0.0001$) using Cu and Zn together was observed.

TABLE 3

Statistical analysis of the 3-factor factorial design assay.
Analysis of Variance for Productivity

| Source | Sum of Squares | Df | Mean Square | F-Ratio | P-Value |
|---|---|---|---|---|---|
| A: Copper | 406.143 | 1 | 406.143 | 350.74 | 0.0000 |
| B: Zinc | 84.6308 | 1 | 84.6308 | 73.09 | 0.0000 |
| C: ctrl_water | 0.626472 | 1 | 0.626472 | 0.54 | 0.4807 |
| AB | 47.7896 | 1 | 47.7896 | 41.27 | 0.0001 |
| AC | 2.49008 | 1 | 2.49008 | 2.15 | 0.1766 |
| BC | 0.438906 | 1 | 0.438906 | 0.38 | 0.5534 |
| Total error | 10.4215 | 9 | 1.15795 | | |
| Total (corr.) | 552.541 | 15 | | | |

R-squared - 98.1139 percent
R-squared (adjusted for d.f.) - 96.8565 percent

Peeling-off was observed in all cultures treated with Zinc at a concentration of 1.5 µM, regardless of whether or not Copper was present.

Subsequent factorial design experiments were carried out in order to study the effect of addition of both Zinc and Copper when the Zinc concentration was decreased (Zn 0.5 µM) and adding other trace elements to the growth medium, such as Manganese, Selenium or Ferric Citrate, which could improve the productivity and the adhesion of the cultures to the substrate.

Figure 3:
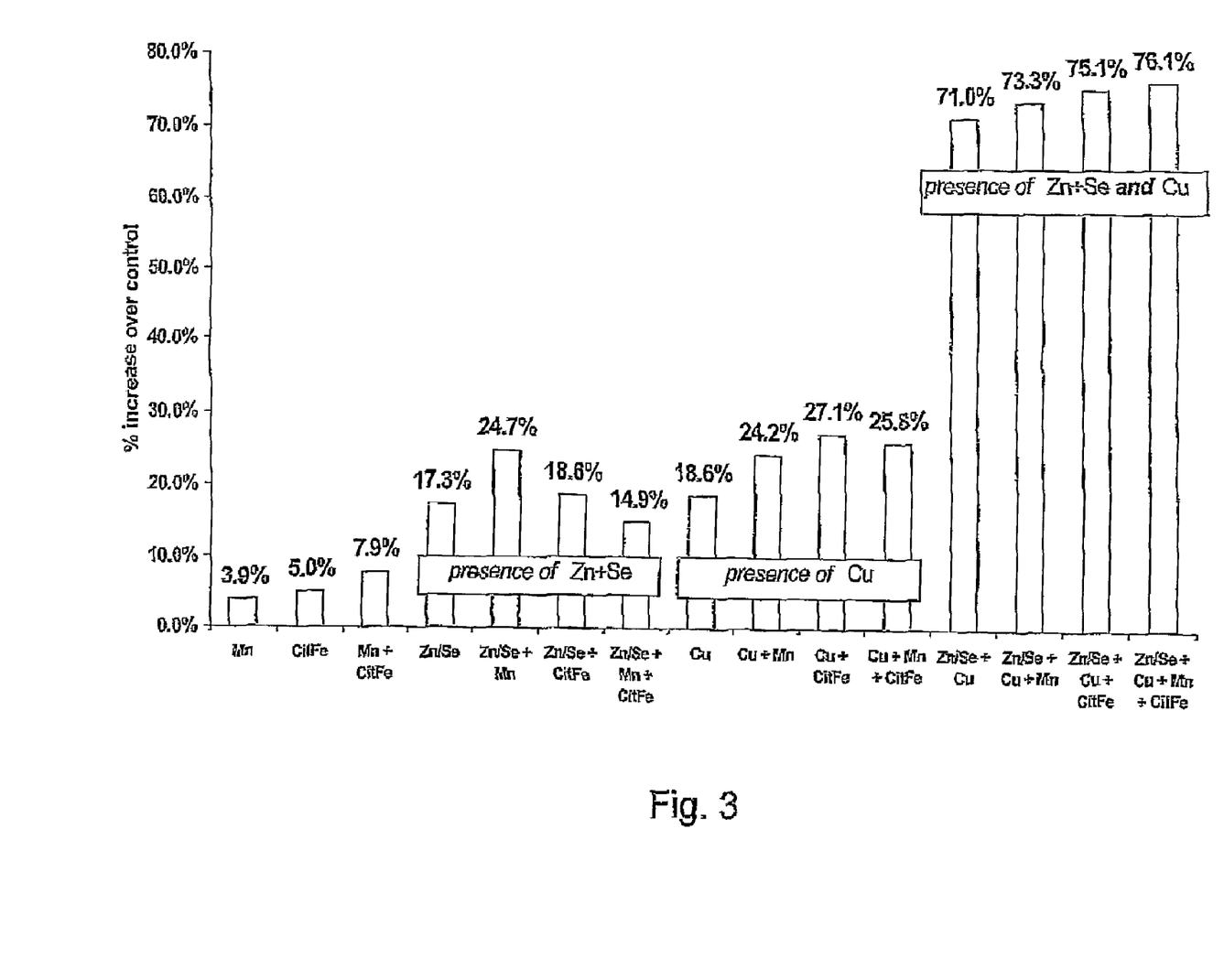
FIG. 3 shows the average values or rhGH productivity increase as compared to control, obtained in the factorial design experiment for testing combinations of zinc (Zn 0.5 µM), copper (Cu 0.02 µM), selenium (Se 0.050 µM), manganese (Mn 0.001 µM) and ferric citrate (4.8 µM)

Continuous growth was reached from a common productivity starting point, around 20 mg rhGH per bottle, with end values close to 70 mg of rhGH/RB compared to 30 mg of rhGH of the control culture with standard DMEM (not shown). The average values for increase in GH productivity (i.e. the productivity measured in mg/RB at day 14) as compared to the control are shown in FIG. 3.

In this series of experiments, the peeling-off phenomenon was diminished.

Amino Acid Addition

An amino acid analysis was carried out in order to determine whether the increase in hGH productivity was limited by the availability of any amino acid. Table 4 shows the percentage of amino acids in harvests after two days in culture, in medium with and without addition of Zinc and Copper.

TABLE 4

Percentage of the concentration of amino acids in the crude medium, harvested after two days in culture, originating from cultures maintained with standard DMEM culture or DMEM supplemented with Zn 0.5 µM, Cu 0.02 µM and ferric citrate 4.8 µM.

| AMINO ACID | STANDARD DMEM | SUPPLEMENTED DMEM |
|---|---|---|
| L-Glutamine | 31% | 13% |
| L-Serine | 28% | 11% |
| L-Cystine | 20% | 13% |
| Remaining L-amino acids | 50%-100% | 39%-86% |

Figure 4:
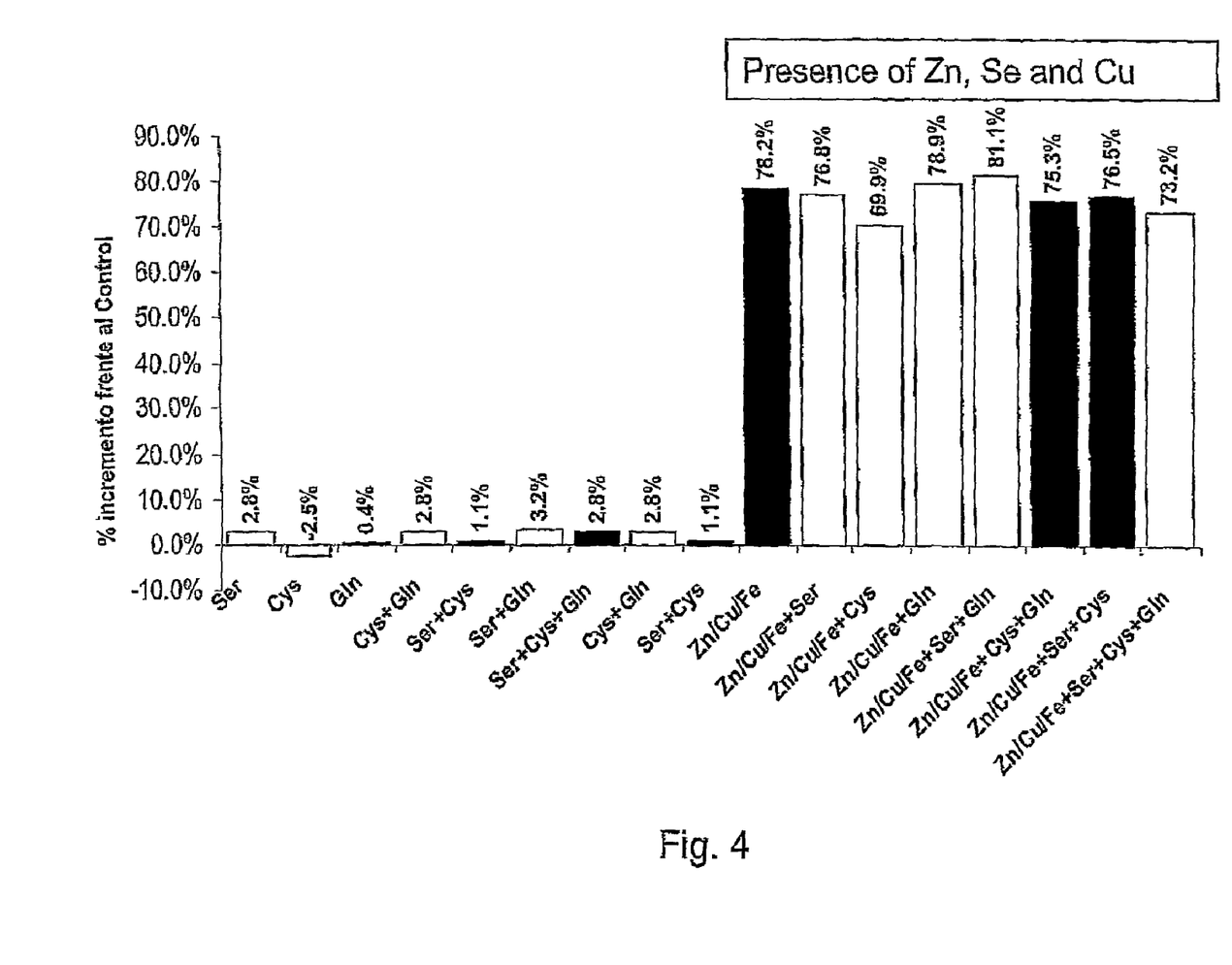
FIG. 4 shows the results of a factorial design experiment to determine the result of a mixture of metallic trace elements (Zn 0.5 µM, Cu 0.02 µM and ferric citrate 4.8 µM) and the amino acids glutamine (Gln 4.8 mM), serine (Ser 0.49 mM) and cystine (Cys 0.29 mM)

A mixture of Copper, Zinc and Ferric citrate (Zn 0.5 µM, Cu 0.02 µM and Ferric Citrate 4.8 µM) was assayed with combinations of those amino acids consumed in the highest proportion: L-glutamine (Gln 4.8 mM), L-serine (Ser 0.49 mM) and L-cystine (Cys 0.29 mM). The results are shown in FIG. 4.

No positive effect on productivity was observed for any of the tested amino acids, neither separately nor combined.

When the metals were added together with the amino acids, only minor effects on productivity were observed: a slight positive effect of glutamine (from 78.2% to 81.1%) and a negative effect of cystine (from 78.2% to 69.9%). Such differences were not considered significant.

The productivity clearly differs between cultures treated with a mixture of metals in DMEM (mean value of about 50 mg rhGH/RB per harvest) from those not comprising the metals (about 30 mg of rhGH/RB per harvest). In view of these results, it was not considered necessary to modify the original amino acid composition of the production medium.

Titration of the Effect of Copper and Zinc

Figure 5:
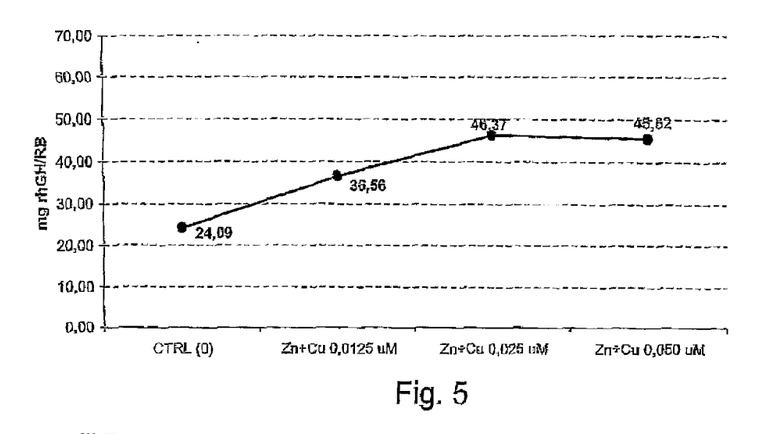
FIG. 5 shows the effect of different concentrations of copper combined with zinc and ferric citrate (Zn 0.5 µM, Fe Citrate 4.8 µM) an rhGH productivity in the DMEM.

In order to measure the optimal concentration of copper, an experiment was performed, keeping the Ferric Citrate concentration (4.8 µM) and Zinc concentration (0.5 µM) constant, and varying the Copper concentrations (FIG. 5).

As shown in FIG. 5, the dose-response experiment confirmed that the optimal supplementation concentration for copper in the DMEM is 25.6 nM when assayed at the indicated Zinc and Ferric Citrate concentrations.

Figure 6:
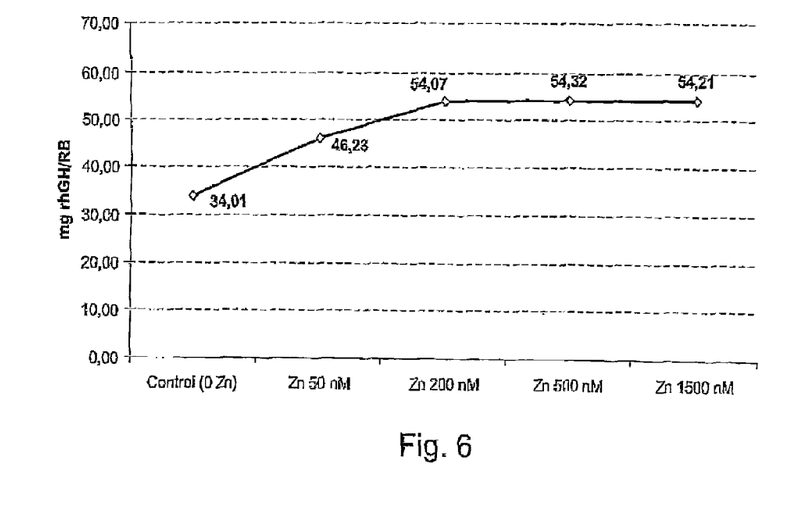
FIG. 6 shows the effect of different concentrations of zinc combined with copper and ferric citrate (Cu 0.02 µM, Fe Citrate 4.8 µM) on rhGH productivity in the DMEM.

In another experiment, the Ferric Citrate concentration (4.8 µM) and Copper (0.025 µM) concentrations were held constant and the Zinc concentration varied (FIG. 6): A maximum productivity level (plateau) was observed with Zinc concentrations above 200 nM, stabilizing the productivity at about 60% over the average control value.

Summary of Results

Figure 7:
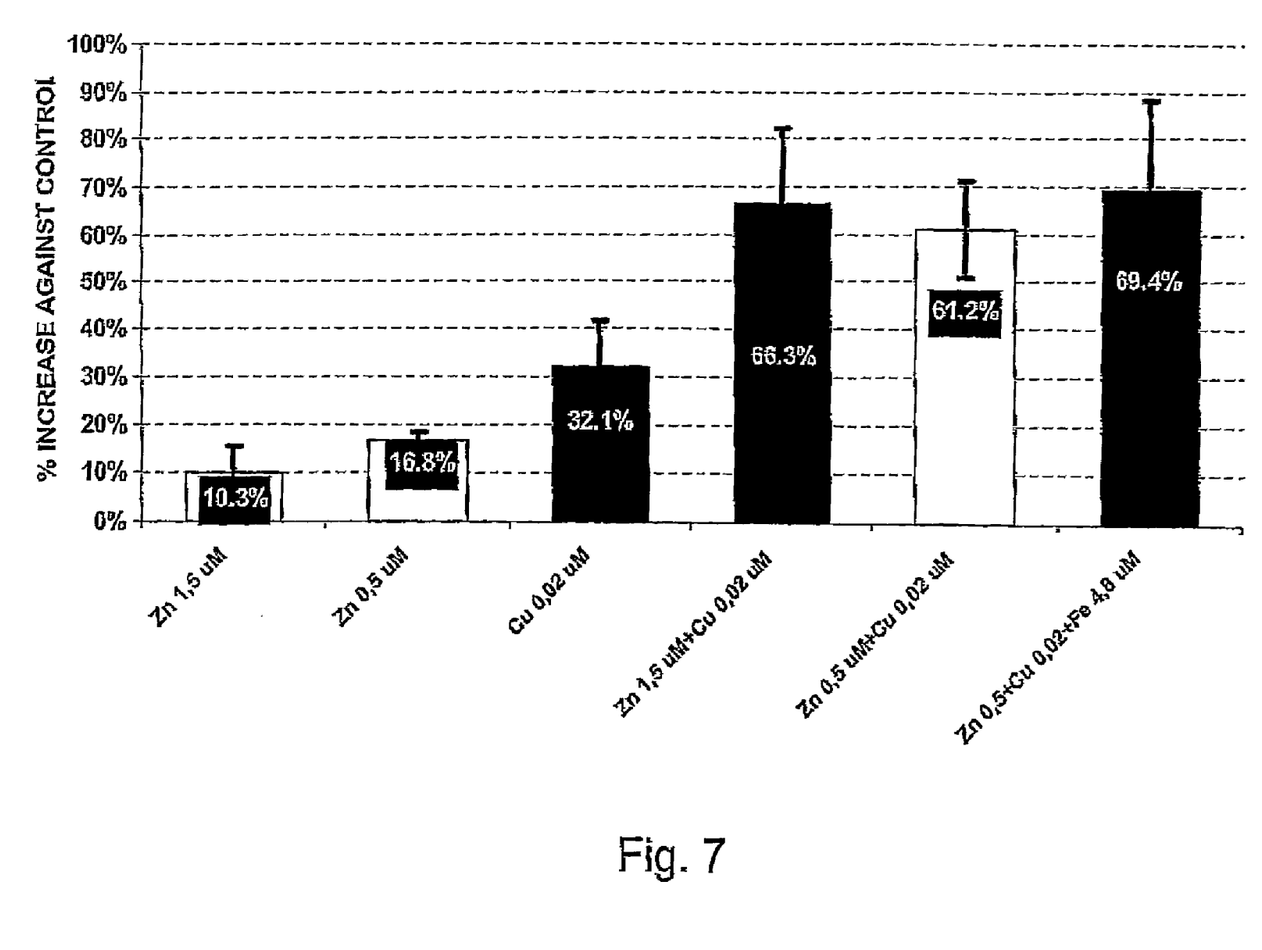
FIG. 7 shows the summary of the effect of the rhGH productivity increase obtained when adding copper, zinc and ferric citrate (Zn: 1.5 and 0.5 µM, Cu: 0.02 µM and ferric citrate: 4.8 µM) as DMEM supplements from different experiments with rhGH-producing C127 cells.

FIG. 7 summarizes the results obtained with Zn and Cu ions in trace concentrations, together or without ferric ions.

The following values were obtained on the basis of data obtained for the increase in productivity by adding metallic trace elements to DMEM medium:

Zinc 1.5 µM: 10.3%±15.0%, Zinc 0.5 µM: 16.8%±1.6%.
Copper 0.02 µM: 32.1%±19.4%,
Zinc 1.5 µM+Copper 0.02 µM: 66.3%±6%
Zinc 0.5 µM+Copper 0.02 µM: 61.2% (±10%)
Zinc 0.5 µM+Copper 0.02 µM+Ferric Citrate 4.8 µM: 69.4%±19%.

In view of these data, the following mixture is optimal as an additive to the DMEM medium:

Copper as copper sulfate ($CuSO_4.5H_2O$) at 25 nM.
Zinc as zinc sulfate ($ZnSO_4.7H_2O$), between 50 mM and 1500 nM, with preferred concentrations ranging from 200 to 500 nM.
Ferric Citrate, at a concentration of 4.8 µM to a final concentration of about 6 µM of the ion, given that Ferric Nitrate is already present in DMEM.

CONCLUSION

The use of Copper, Zinc and Ferric ions in trace amounts as supplements to DMEM medium increased rhGH productivity by more than 50% as compared to standard DMEM.

REFERENCES

1. Altschul S F et al, J Mol Biol, 215, 403-410, 1990.
2. Arnold et al. US 2003/0153042
3. Ausubel et al., Current Protocols in Molecular Biology, supra, Interscience, N.Y., §§6.3 and 6.4 (1987, 1992).
4. Altschul S F et al, Nucleic Acids Res., 25:389-3402, 1997,
5. Becker at al, Biotechnol. Appl. Biochem. 10:326 (1988)
6. Bewly et al, Int. J. Peptide and Protein Res. 4:281-287 (1972)
7. Blum et al. U.S. Pat. No. 6,399,381
8. Bohak et al. 1987 Bohak Z, Kadouri A et al. (1987) "Novel anchorage matrices for suspension culture of mammalian cells" Biopolymers. 26 Suppl:S205-213.

9. Carter M J, Facklam T J, Long P C, Scotland R A, Dev, Biol. Stand, 1989; 70:101-7.
10. Chen et al, Genomics 4:479-497 (1989)
11. Ciccarone et al. US 2003/0096414
12. Cleveland et al., U.S. Pat. No. 4,767,704
13. Darfler U.S. Pat. No. 5,045,468
14. DeNoto et al, Nucleic Acids Res. 9:3719 (1981)
15. Devereux J et al, Nucleic Acids Res, 12, 387-395, 1984.
16. Gertler et al, Endocrinology 118:720 (1986)
17. Goeddel et al Nature, 281:544 (1979)
18. Graff et al, J. Biol. Chem. 257:2365 (1982)
19. Grantham et al., Science, Vol. 185, pp. 862-864 (1974).
20. Hsiung et al, Biotechnology 7:267 (1989)
21. Inlow et al. U.S. Pat. No. 6,046,728
22. Jorgensson et al, Pharmacol. Toxicol. 63:129 (1988)
23. Lewis et al, Endocrinology 101:1587 (1977)
24. Lewis et al, J. Biol. Chem. 253:2679 (1978)
25. Lewis et al, Endocrinology 104:1256 (1979)
26. Lewis et al, Biochem. Biophys. Res. Comm. 92:511 (1980)
27. Lewis et al, J. Biol. Chem. 256:11645 (1981)
28. Lindner M C 1991. Biochemistry of copper. New York, Plenum press (textbook)
29. Martial et al, Science 205:602-607 (1979)
30. Moore et al, Endocrinology 122:2920 (1988)
31. Novick, P. Kim, S-H, Fantuzzi, G, Reznikov, L, Dinarello, C, and Rubinstein, M (1999). Immunity 10, 127-136,
32. Oka M S, Rupp R G. Bioprocess Technol. 1990; 10:71-92
33. Pearson, Methods Enzymol. 1990; 183:63-98.
34. Petti S A, Lages A C et al. (1994) "Three-dimensional mammalian cell growth on nonwoven polyester fabric disks" Biotechnol Prog. 10(5):548-550.
35. Puck at al., J. Exp. Med. 108, 945, 1958
36. Renner et al., U.S. Pat. No. 5,811,299
37. Singh et al, Endocrinology 94:883 (1974)
38. Thorlacius-Ussing, Neuroendocrinology 43:233 (1987)
39. Vallee S L and Falchuk K H 1993. The biochemical basis of zinc physiology. Physiological reviews 73, 79-118.
40. EP 274 445
41. EP 314317 A1
42. EP 0 325 224 A2
43. WO 01/16294

The invention claimed is:

1. A process for the production of growth hormone comprising the step of culturing cells of a cell line expressing growth hormone in a cell culture medium free of components derived from animal serum, wherein the medium comprises ferric ions at a concentration of 5 µM or 6 µM, zinc at a concentration ranging from 0.2 µM to 0.5 µM and copper at a concentration of 25 nM.

2. The process according to claim 1, wherein the medium comprises zinc at a concentration of 0.2 µM or 0.5 µM.

3. The process according to claim 1, wherein the zinc is provided as zinc sulfate.

4. The process according to claim 2, wherein the zinc is provided as zinc sulfate.

5. The process according to claim 1, wherein the copper is provided as copper sulfate.

6. The process according to claim 1, wherein the ferric ions are provided in the form of ferric citrate and/or ferric nitrate.

7. The process according to claim 1, wherein the medium comprises: zinc at a concentration ranging from 0.2 µM to 0.35 µM, copper at a concentration of 25 µM and ferric ions at a concentration of 5 µM or 6 µM.

8. The process according to claim 1, wherein the medium is Dulbecco's Modified Eagle's Medium (DMEM).

9. The process according to claim 1, wherein the growth hormone is expressed under the control of a metallothionein (MT) promoter.

10. The process according to claim 9, wherein the metallothionein promoter is the mouse MT-1 promoter.

11. The process according to claim 1, further comprising collecting the growth hormone from the cell culture.

12. The process according to claim 11, further comprising purifying the growth hormone.

13. The process according to claim 12, further comprising formulating the purified growth hormone with a pharmaceutically acceptable carrier to obtain a pharmaceutical composition.

14. The process according to claim 1, wherein the growth hormone is human growth hormone.

15. The process according to claim 1, wherein the cells are mouse C127 cells.

16. A process for the production of growth hormone comprising the step of culturing cells of a cell line expressing growth hormone in a cell culture medium free of components derived from animal serum, wherein the medium comprises Dulbecco's Modified Eagle's Medium supplemented with ferric ions at a concentration of 4.8 µM, zinc at a concentration of 0.5 nM and copper at a concentration of 25 µM.

17. The process according to claim 16, wherein the zinc is provided as zinc sulfate.

18. The process according to claim 16, wherein the copper is provided as copper sulfate.

19. The process according to claim 16, wherein the ferric ions are provided in the form of ferric citrate.

20. A process for the production of growth hormone comprising the step of culturing cells of a cell line expressing growth hormone in a cell culture medium free of components derived from animal serum, wherein the medium comprises Dulbecco's Modified Eagle's Medium supplemented with:
   a) zinc at a concentration of 1.5 µM and copper at a concentration of 0.02 µM; or
   b) zinc at a concentration of 0.5 µM and copper at a concentration of 0.02 µM.

21. The process according to claim 20, wherein the zinc is provided as zinc sulfate.

22. The process according to claim 20, wherein the copper is provided as copper sulfate.

23. The process according to claim 20, wherein the Dulbecco's Modified Eagle's Medium is supplemented with zinc at a concentration of 1.5 µM and copper at a concentration of 0.02 µM.

24. The process according to claim 20, wherein the Dulbecco's Modified Eagle's Medium is supplemented with zinc at a concentration of 0.5 µM and copper at a concentration of 0.02 µM.

* * * * *

UNITED STATES PATENT AND TRADEMARK OFFICE
CERTIFICATE OF CORRECTION

PATENT NO.        : 7,709,229 B2
APPLICATION NO.   : 11/576277
DATED             : May 4, 2010
INVENTOR(S)       : Jose Casatorres Hernandez and Carlos Martin Piera It is certified that error appears in the above-identified patent and that said Letters Patent is hereby corrected as shown below:

Column 1,
Line 50, "of, cattle" should read --of cattle--.
Line 60, "further compounds." should read --further compounds:--.

Column 3,
Line 10, "crosslinking" should read --crosslining--.
Line 49, "(newly" should read --(Bewly--.

Column 4,
Lines 22-23, "or greater the amount" should read --or greater than the amount--.
Line 24, "22 kb" should read --22 kD--.

Column 5,
Line 16, "electorphoretically" should read --electrophoretically--.
Line 61, "U.S. Pat. No. 5,324,666" should read --U.S. Pat. No. 5,324,656--.

Column 7,
Line 16, "an rhGH" should read --on rhGH--.

Column 9,
Line 30, "LFA3/IgG1" should read --LFA-3/IgG1--.

Column 12,
Line 39, "blood colt reconstitution" should read --blood cell reconstitution--.
Lines 66-77, "conventional methods steps" should read --conventional method steps--.

Column 13,
Line 10, "experimentations without" should read --experimentation, without--.
Line 13, "meaning an range" should read --meaning and range--.

Signed and Sealed this

Twenty-ninth Day of June, 2010

David J. Kappos
*Director of the United States Patent and Trademark Office*

Column 15,
Line 55, "obtained form" should read --obtained from--.
Lines 58-59, "(K[Cr(SO$_6$H$_4$)$_2$(H$_2$O)]·6H$_2$O)" should read
 --(K[Cr(SO$_6$H$_4$)$_2$(H$_2$O)$_2$]·6H$_2$O)--.

Column 17,
Line 38, "TFA (3.08%" should read --TFA 0.08%--.

Column 18,
Line 14, "(K[Cr(SO$_3$H$_4$)$_2$(H$_2$O)$_2$]·6H$_2$O)" should read
 --(K[Cr(SO$_6$H$_4$)$_2$(H$_2$O)$_2$]·6H$_2$O)--.

Column 20,
Line 33, "± 6%" should read --± 16%--.
Line 41, "50 mM" should read --50 nM--.

Column 21,
Line 14, "U.S. Pat. No. 6,046,728" should read --U.S. Pat. No. 6,048,728--.
Line 37, "Vallee S L" should read --Vallee B L--.

Column 22,
Line 3, "of 25 µM" should read --of 25 nM--.
Line 30, "0.5 nM and copper at a concentration of 25 µM" should read
 --0.5 µM and copper at a concentration of 25 nM--.